(12) United States Patent
Ahmed et al.

(10) Patent No.: US 7,390,503 B1
(45) Date of Patent: Jun. 24, 2008

(54) ONDANSETRON ORALLY DISINTEGRATING TABLETS

(75) Inventors: Salah U. Ahmed, New City, NY (US); Sudhir R. Gorukanti, Harriman, NY (US); Tahseen A. Chowdhury, Washington Township, NJ (US)

(73) Assignee: Barr Laboratories, Inc., Pomona, NY (US)

( * ) Notice: Subject to any disclaimer, the term of this patent is extended or adjusted under 35 U.S.C. 154(b) by 892 days.

(21) Appl. No.: 10/923,021

(22) Filed: Aug. 23, 2004

Related U.S. Application Data

(60) Provisional application No. 60/497,063, filed on Aug. 22, 2003.

(51) Int. Cl.
  *A61K 9/20* (2006.01)
  *A61K 9/14* (2006.01)
  *A61K 9/50* (2006.01)

(52) U.S. Cl. ...................... 424/464; 424/465; 424/489; 424/499

(58) Field of Classification Search ....................... None
See application file for complete search history.

(56) References Cited

U.S. PATENT DOCUMENTS

| | | | |
|---|---|---|---|
| 3,885,026 A | 5/1975 | Heinemann et al. | |
| 4,134,943 A | 1/1979 | Knitsch et al. | |
| 4,695,578 A | 9/1987 | Coates et al. | |
| 4,721,720 A | 1/1988 | Wootton et al. | |
| 4,725,615 A | 2/1988 | Coates et al. | |
| 4,739,072 A | 4/1988 | Oxford et al. | |
| 4,753,789 A | 6/1988 | Tyers et al. | |
| 4,783,478 A | 11/1988 | Wootton et al. | |
| 4,832,956 A | 5/1989 | Gergely et al. | |
| 4,929,632 A | 5/1990 | Tyers et al. | |
| 4,957,609 A | 9/1990 | Godfrey et al. | |
| 5,073,374 A | 12/1991 | McCarty | |
| 5,112,616 A | 5/1992 | McCarty | |
| 5,178,878 A | 1/1993 | Wehling et al. | |
| 5,225,197 A | 7/1993 | Bolt et al. | |
| 5,225,202 A | 7/1993 | Hodges et al. | |
| 5,240,954 A | 8/1993 | Tyers et al. | |
| 5,344,658 A | 9/1994 | Collin | |
| 5,416,221 A | 5/1995 | Bod et al. | |
| 5,425,950 A * | 6/1995 | Dandiker et al. | |
| 5,464,632 A | 11/1995 | Cousin et al. | |
| 5,470,868 A | 11/1995 | Young | |
| 5,478,949 A | 12/1995 | Bod et al. | |
| 5,501,861 A | 3/1996 | Makino et al. | |
| 5,503,846 A | 4/1996 | Wehling et al. | |
| 5,506,248 A | 4/1996 | Nikfar et al. | |
| 5,576,014 A | 11/1996 | Mizumoto et al. | |
| 5,578,628 A | 11/1996 | Tyers et al. | |
| 5,587,180 A | 12/1996 | Allen, Jr. et al. | |
| 5,595,761 A | 1/1997 | Allen, Jr. et al. | |
| 5,607,697 A | 3/1997 | Alkire et al. | |
| 5,622,720 A | 4/1997 | Collin | |
| 5,624,687 A | 4/1997 | Yano et al. | |
| 5,635,210 A | 6/1997 | Allen, Jr. et al. | |
| 5,712,302 A | 1/1998 | Young | |
| 5,725,884 A | 3/1998 | Sherwood et al. | |
| 5,731,339 A | 3/1998 | Lowrey | |
| 5,747,068 A | 5/1998 | Mendizabal | |
| 5,776,491 A | 7/1998 | Allen, Jr. et al. | |
| 5,807,576 A | 9/1998 | Allen, Jr. et al. | |
| 5,837,285 A | 11/1998 | Nakamichi et al. | |
| 5,837,292 A | 11/1998 | Dijkgraaf et al. | |
| 5,854,270 A | 12/1998 | Gambhir et al. | |
| 5,922,749 A | 7/1999 | Tyers et al. | |
| 5,948,438 A | 9/1999 | Staniforth et al. | |
| 5,955,107 A | 9/1999 | Augello et al. | |
| 5,955,488 A | 9/1999 | Winterborn | |
| 5,958,453 A | 9/1999 | Ohno et al. | |
| 5,962,494 A | 10/1999 | Young | |
| 5,977,099 A | 11/1999 | Nickolson | |
| 5,981,563 A | 11/1999 | Lowrey | |
| 6,024,981 A | 2/2000 | Khankari et al. | |
| 6,063,802 A | 5/2000 | Winterborn | |
| 6,083,531 A | 7/2000 | Humbert-Droz et al. | |
| 6,106,861 A | 8/2000 | Chauveau et al. | |
| 6,126,969 A | 10/2000 | Shah et al. | |
| 6,149,938 A | 11/2000 | Bonadeo et al. | |
| 6,150,353 A | 11/2000 | Broekkamp et al. | |
| 6,155,423 A | 12/2000 | Katzner et al. | |
| 6,159,499 A | 12/2000 | Seth | |

(Continued)

FOREIGN PATENT DOCUMENTS

EP 0 839 526 A2 5/1998

(Continued)

OTHER PUBLICATIONS

Bi, Y.X., et al., "Evaluation of rapidly disintegrating tablets prepared by a direct compression method," *Drug Dev. Ind. Pharm.* 25:571-581, Marcel Dekker, Inc. (1999).

(Continued)

*Primary Examiner*—Humera N Sheikh
(74) *Attorney, Agent, or Firm*—Sterne, Kessler, Goldstein & Fox P.L.L.C.

(57) ABSTRACT

An ondansetron solid orally disintegrating dosage form for oral administration having at least one first water-dispersible component or water-insoluble cellulose derivative, a component having a —CHOH functional group, a disintegrating agent and at least one lubricant is provided. The dosage form can comprise ondansetron, a hydrophilic polymer such as microcrystalline cellulose, a component having a —CHOH functional group such as mannitol or xylitol and a disintegrating agent such as crospovidone. The lubricant may be a mixture of magnesium stearate, sodium stearyl fumarate and colloidal silicon dioxide. The present invention provides a non-effervescent tablet comprising the ondansetron dosage form. Another aspect of the invention is the treatment of emesis such as nausea and vomiting caused by cancer chemotherapy and radiation by the administration of the ondansetron formulation of the present composition. Finally, a process of forming an ondansetron disintegrating tablet using the ondansetron dosage form is disclosed.

11 Claims, 5 Drawing Sheets

U.S. PATENT DOCUMENTS

Figure 1:
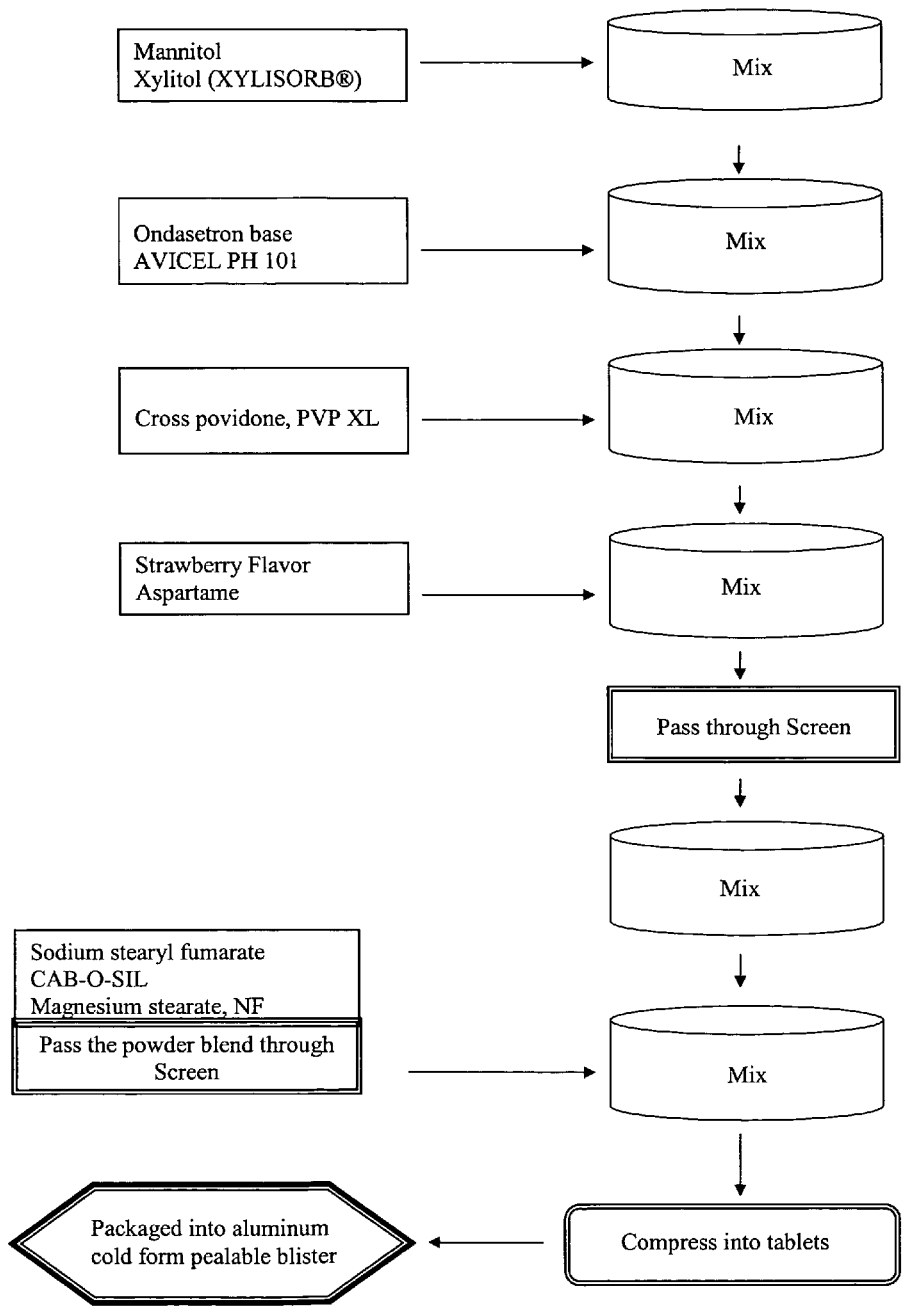

| | | | |
|---|---|---|---|
| 6,166,061 | A | 12/2000 | Lowrey |
| 6,200,604 | B1 | 3/2001 | Pather et al. |
| 6,280,770 | B1 | 8/2001 | Pather et al. |
| 6,281,207 | B1 | 8/2001 | Richter et al. |
| 6,294,196 | B1 | 9/2001 | Gabel et al. |
| 6,294,198 | B1 | 9/2001 | Vilkov |
| 6,299,904 | B1 | 10/2001 | Shimizu et al. |
| 6,316,029 | B1 | 11/2001 | Jain et al. |
| 6,328,994 | B1 | 12/2001 | Shimizu et al. |
| 6,350,470 | B1 | 2/2002 | Pather et al. |
| 6,365,182 | B1 | 4/2002 | Khankari et al. |
| 6,368,625 | B1 | 4/2002 | Siebert et al. |
| 6,372,253 | B1 | 4/2002 | Daggy et al. |
| 6,372,255 | B1 | 4/2002 | Saslawski et al. |
| 6,375,982 | B1 | 4/2002 | Cherukuri |
| 6,384,020 | B1 | 5/2002 | Flanner et al. |
| 6,388,091 | B1 | 5/2002 | Lee et al. |
| 6,406,717 | B2 | 6/2002 | Cherukuri |
| 6,410,054 | B1 | 6/2002 | Thosar et al. |
| 6,448,293 | B1 | 9/2002 | Andrews et al. |
| 6,495,165 | B1 | 12/2002 | Thosar et al. |
| 6,576,651 | B2 | 6/2003 | Bandyopadhyay et al. |
| 6,589,556 | B2 | 7/2003 | Cherukuri |
| 6,610,747 | B2 | 8/2003 | Adam et al. |
| 6,630,504 | B2 | 10/2003 | Andrews et al. |
| 6,645,988 | B2 | 11/2003 | Phillips |
| 6,660,382 | B2 | 12/2003 | Nouri et al. |
| 6,723,348 | B2 | 4/2004 | Faham et al. |
| 6,800,652 | B2 | 10/2004 | Andrews et al. |
| 6,814,978 | B2 | 11/2004 | Bunick et al. |
| 2001/0053778 | A1 | 12/2001 | Hoover et al. |
| 2002/0001617 | A1 | 1/2002 | Lee et al. |
| 2002/0071864 | A1* | 6/2002 | Kim et al. |
| 2002/0091129 | A1 | 7/2002 | Boolell |
| 2002/0122823 | A1 | 9/2002 | Bunick et al. |
| 2002/0123504 | A1 | 9/2002 | Redmon et al. |
| 2002/0147232 | A1 | 10/2002 | Sundgreen et al. |
| 2002/0187188 | A1 | 12/2002 | Cherukuri |
| 2003/0022912 | A1 | 1/2003 | Martino et al. |
| 2003/0035833 | A1 | 2/2003 | He |
| 2003/0054037 | A1 | 3/2003 | Babcock et al. |
| 2003/0170309 | A1 | 9/2003 | Babcock et al. |
| 2003/0224043 | A1 | 12/2003 | Appel et al. |
| 2003/0228358 | A1 | 12/2003 | Perlman et al. |
| 2003/0229027 | A1 | 12/2003 | Eissens et al. |
| 2004/0058896 | A1 | 3/2004 | Dietrich et al. |
| 2004/0122106 | A1 | 6/2004 | Ohta et al. |
| 2004/0138263 | A1 | 7/2004 | D'Angio et al. |
| 2004/0142034 | A1 | 7/2004 | Thor et al. |
| 2005/0169986 | A1 | 8/2005 | Tian et al. |
| 2005/0208141 | A1 | 9/2005 | Farber et al. |

FOREIGN PATENT DOCUMENTS

| | | |
|---|---|---|
| EP | 1 161 941 A1 | 12/2001 |
| EP | 1 203 580 A1 | 5/2002 |
| WO | WO 87/05804 | 10/1987 |
| WO | WO 98/53798 | 12/1998 |

OTHER PUBLICATIONS

Bi, Y.X., et al., "Preparation and evaluation of a compressed tablet rapidly disintegrating in the oral Cavity," *Chem. Pharm. Bull.* 44:2121-2127, Pharmaceutical Society of Japan (1996).

Davidson, N., et al., "Comparison of an orally disintegrating ondansetron tablet with the conventional ondansetron tablet for cyclophosphamide-induced emesis in cancer patients: A multi-center, double-masked study," *Clin. Ther.* 21:492-502, Elsevier Science, Inc. (1999).

El-Arini, S.K. and Clas, S.D., "Evaluation of disintegration testing of different fast dissolving tablets using the texture analyzer," *Pharm. Dev. Technol.* 7:361-371, Marcel Dekker, Inc. (2002).

Gan, T.J., et al., "Ondansetron orally disintegrating tablet versus placebo for the prevention of postdischarge nausea and vomiting after ambulatory surgery," *Anesth. Analg.* 94:1199-1200, International Anesthesia Research Society (2002).

Habib, W., et al., "Fast-dissolve drug delivery systems," *Critical Reviews™ in Therapeutic Drug Carrier Systems* 17:61-72, Begell House, Inc. (2000).

Hom, F.S. and Miskel, J.J., "Enhanced dissolution rates for a series of drugs as a function of dosage form design," *Intl. J. Law Sci.* 8:18-26, International Academy of Law and Science (1971).

Ishikawa, T., et al., "Preparation of rapidly disintegrating tablet using new types of microcrystalline cellulose (PH-M Series) and low substituted-hydroxypropylcellulose or spherical sugar granules by direct compression method," *Chem. Pharm. Bull.* 49:134-139, Pharmaceutical Society of Japan (2001).

Koizumi, K., et al., "New method of preparing high-porosity rapidly saliva soluble compressed tablets using mannitol with camphor, a subliming material," *Intl. J. Pharm.* 152:127-131, Elsevier Science B.V. (1997).

LeBourgeois, J.P., et al., "Efficacy of an ondansetron orally disintegrating tablet: A novel oral formulation of this 5-$HT_3$ receptor antagonist in the treatment of fractionated radiotherapy-induced nausea and emesis," *Clin. Oncol.* 11:340-347, The Royal College of Radiologists (1999).

Lehoczky, O., et al., "Freeze dried ondansetron: first observations with the fast dissloving oral anitemetic Zofran™ Zydis™ for the prophylaxis of the cisplatin-induced emesis in gynecological cancer patients," *Neoplasma* 49:126-128, Cancer Research Institute (2002).

Liang, A.C. and Chen, L.H., "Fast-dissolving intraoral drug delivery systems," *Expert Opinion on Therapeutic Patents* 11:981-986, Ashley Publications Ltd. (2001).

Lowenthal, W., "Mechanism of action of tablet disintegrants," *Pharmaceutica Acta Helvetiae* 48:589-609, Elsevier B.V. (1973).

Massimo, G., et al., "Disintegration propensity of tablets evaluated by means of disintegrating force kinetics," *Pharm. Dev. Technol.* 5:163-169, Marcel Dekker, Inc. (2000).

Nakagami, H. and Nada, M., "The use of micronized cellulose disintegrants as insoluble swellable matrices for sustained-release tablets," *Drug Design and Delivery* 7:321-332, Harwood Academic Publishers GmbH (1991).

Sastry, S.V., et al., "Recent technological advances in oral drug delivery—a review," *Pharm. Sci. Technol. Today* 3:138-145, Elsevier Science (2000).

Watanabe, Y., et al., "New compressed tablet rapidly disintegrating in saliva in the mouth using crystalline cellulose and a disintegrant," *Biol. Pharm. Bull.* 18:1308-1310, Pharmaceutical Society of Japan (1995).

Co-pending U.S. Appl. No. 10/902,836, inventors Ahmed, S., et al., filed Aug. 2, 2004 (Not Published).

Co-pending U.S. Appl. No. 11/048,120, inventors Ahmed, S., et al., filed Feb. 2, 2005 (Not Published).

Bogner, R. and Wilkosz, M., "Fast-dissolving Tablets," *U.S. Pharmacist* 27:34-43, Jobson Medical Information, LLC (Mar. 2002) Published online Sep. 13, 2002: http://www.uspharmacist.com/oldformat.asp?url=newlook/files/feat/fastdissolving.htm, last accessed Sep. 27, 2006.

Borsadia, S.B. et al., "Quick-dissolving films—a novel approach to drug delivery" *Drug Delivery Tech.* 3, Drug Delivery Technology (2003) Accessed online: http://www.drugdeliverytech.com/cgi-bin/articles.cgi?idArticle=138, last accessed Sep. 27, 2006.

Brown, D. "Orally disintegrating tablets—taste over speed," *Drug Delivery Tech.* 3, Drug Delivery Technology (Sep. 2003) Accessed online: http://www.drugdeliverytech.com/cgi-bin/articles.cgi?idArticle=164, last accessed Sep. 27, 2006.

Caramella, C. et al., "The Role of Swelling in the Disintegration Process," *Int. J. Pharm. Tech & Prod. Mfr.*, 5(2):1-5, Child Wall University Press Ltd. (1984).

Caramella, C. et al., "Disintegrants in Solid Dosage Forms," *Drug Development and Industrial Pharmacy*, 16(17):2561-2577, Marcel Dekker, Inc. (1990).

Dobetti, L., "Fast-melting tablets: developments and technologies," *Pharm. Tech.: Drug Delivery* 2001:44-50, Advanstar Communications, Inc. (2001) Accessed online: http://www.pharmtech.com/pharmtech/data/articlestandard/pharmtech/512001/5137/article.pdf last accessed Sep. 27, 2006.

Klancke, J. "Dissolution testing of orally disintegrating tablets," *Dissolution Tech. 10*, Dissolution Technologies, Inc. (May 2003) Accessed online: http://www.dissolutiontech.com/DTresour/0503art/DT0503art1.pdf, last accessed Sep. 27, 2006.

Mirtazapine Orally Disintegrating Tablets, The Electronic Orange Book, The United State Food and Drug Administration (15 mg and 30 mg, Dec. 17, 2003; 45 mg, Feb. 28, 2006) Accessed online: http://www.accessdata.fda.gov/scripts/cder/ob/docs/obdetail.cfm?Appl_No=076307&TABLE1=OB_Rx, last accessed: Mar. 26, 2008.

Label and Packaging for Mirtazapine Orally Disintegrating Tablets (15 mg and 30 mg), Barr Laboratories, Inc. (Dec. 17, 2003).

* cited by examiner

ONDANSETRON ORALLY DISINTEGRATING TABLETS

The application claims the benefit of U.S. Provisional Application No. 60/497,063, filed Aug. 22, 2003, which is herein incorporated by reference in its entirety.

BACKGROUND OF THE INVENTION

1. Field of the Invention

The present invention generally relates to non-effervescent, solid dosage forms adapted for oral administration of 1,2,3,9-tetrahydro-9-methyl-3-[(2-methyl-1H-imidazol-1-yl)methyl]-4H-carbazol-4-one (ondansetron) as an anti-emetic active ingredient for the prevention of nausea and vomiting. Particularly, the invention relates to solid dosage forms containing ondansetron in the form of orally disintegrating tablets.

2. Background Art

U.S. Pat. No. 4,695,578 discloses that ondansetron is a highly selective and potent antagonist of 5-hydroxytryptamine (5-HT) at $5HT_3$ receptors in the gastrointestinal tract, where it blocks both sites of serotonin-induced nausea and vomiting (emesis). Emesis is a frequent side effect of cancer chemotherapeutic agents, such as cisplatin. Emesis causes serious problems in cancer chemotherapy, and in some patients emesis is so severe that therapy must be discontinued. Anti-emetic agents are therefore often administered in order to alleviate this side effect of cancer chemotherapy. Ondansetron, together with its physiologically acceptable salts is used in the treatment of a variety of conditions ameliorated by administration of $5HT_3$ receptor antagonists, such as emesis, including the nausea and vomiting induced by cancer chemotherapy and radiotherapy.

Consequently, ondansetron can produce a significant reduction, or a complete inhibition of nausea and vomiting in patients treated with cancer chemotherapeutics of moderate- or high-emetic potential. Similarly, the compound prevents radiation-induced nausea and emesis.

Administration of oral or injectable free base and salts of ondansetron, e.g., hydrochloride dihydrate, is disclosed in U.S. Pat. Nos. 4,753,789; 4,929,632; 5,955,488 and 6,063,802.

Oral administration in the form of a conventional tablet, pill or capsule constitutes a generally preferred route for administration of pharmaceuticals since this route is generally convenient and acceptable to patients. Unfortunately, such compositions may be associated with certain disadvantages, particularly in the treatment of pediatric or geriatric patients, who may dislike or have difficulty in swallowing such compositions, or where administration of a conventional tablet, pill or capsule is not feasible. It is highly desirable, particularly in the treatment of acute conditions, that pharmaceutical compositions have a rapid and consistent onset of action combined with sustained activity and good bioavailability. Rapid absorption can be achieved by parenteral injection but this is unacceptable to many patients, particularly if the drug is to be self-administered without direct medical supervision.

Preparations for oral administration normally come in the form of a tablet, granule, powder or solution. However, since a solid preparation need be swallowed with some water, the elderly, infants and patients who have difficulty in swallowing prefer dosage forms such as a liquid preparation or a rapidly disintegrating tablet which easily disintegrates by the action of saliva.

Although certain liquid dosage forms may be suitable for the elderly, infants or patients who have difficulty in swallowing, they have shortcomings such as difficulty in handling, especially in measuring an accurate dosage, and in that they are not suitable for drugs which are unstable in a moist environment.

Orally disintegrating solid dosage forms have significant advantages over other dosage forms, particularly for patients who cannot, or will not, swallow a tablet or capsule. Moreover, solid dosage forms are far more convenient than liquids. Formulations such as porous tablets, chewable tablets, non-chewable tablets, freeze-dried dosage forms and dosage forms containing microparticles and effervescent couples are disclosed in U.S. Pat. Nos. 3,885,026, 4,134,943, 5,225,197, 5,178,878, 5,955,488, and 6,024,981. Some of the dosage forms disclosed in the listed patents are suitable for some patients, however, the dosage forms pose significant problems in terms of production, storage, transport and during consumer usage. The dosage forms are also significantly more costly to produce, e.g., freeze-drying processes are expensive and time-consuming. In addition, the effectiveness of a freeze-drying process depends on the physico-chemical parameters of the active substances used. For certain active substances, especially those having a high solubility in water, it is difficult or impossible to apply a freeze-drying process. Finally, the development of units with high doses (up to 500 mg or even 1000 mg) of active ingredients and/or combinations of active ingredients is difficult with freeze-drying.

In addition, freeze-dried tablets are so fragile that the matrix material must be formed by freeze-drying in an individual tablet-sized container. While the use of an effervescent couple in combination with microparticles may overcome the need for such extreme measures, the need to minimize in-mouth disintegration times still requires the use of non-traditional packaging and processing methodology. For example, normal conveyors such as vibratory conveyors or bulk hoppers common in the pharmaceutical industry could not be used, as these high-speed, high-volume devices tend to cause damage to the resulting tablets. Similarly, the resulting tablets cannot be stored on a hopper after tableting but before packaging. They can not be packaged in a conventional, multi-tablet bottle, individual foil pouches or traditional blister packaging due to high likelihood of tablet breakage. This can seriously interfere with the processing efficiencies of high-volume presses.

There exists a need in the art for alternatives to expensive manufacturing processes, e.g., freeze drying, to produce orally disintegrating ondansetron tablets, which are bioequivalent to the existing Zofran orally disintegrating tablets.

BRIEF SUMMARY OF THE INVENTION

The present invention provides a non-effervescent, solid orally disintegrating dosage form adapted for oral administration to a mammal, such as a human, of ondansetron composition having at least one hydrophilic component comprising a first-water dispersible component, a component having a —CHOH functional group and a water-insoluble component, optionally a lubricant and optionally a sweetener. Useful dosage forms include ondansetron orally disintegrating tablets. In some embodiments, the dosage forms provide for greater than 75 percent dissolution at thirty minutes when measured in a medium of 500 mL of 0.01 N HCl and a paddle speed of 50 rpm. In some embodiments, the dosage forms provide for greater than 95 percent dissolution at five minutes, when measured in a medium of 500 mL of 0.01 N HCl and a paddle speed of 50 rpm. A representative dosage form comprises ondansetron, microcrystalline cellulose, aspartame, crospovidone, mannitol, colloidal silicon dioxide, magnesium stearate, sodium stearyl fumarate and xylitol. In addition, the present invention provides a non-effervescent tablet comprising the ondansetron composition. The dosage forms can be used for the treatment of emesis such as nausea and vomiting caused by cancer chemotherapy and radiation or mental disorders. Finally, a process of forming an ondansetron disintegrating tablet is disclosed.

The present invention relates to dosage forms of ondansetron, a compound having the following chemical formula:

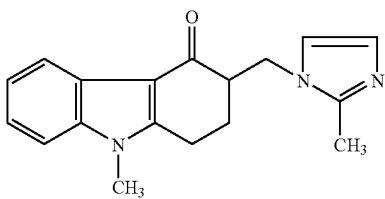

wherein the formulation of this compound with certain inert ingredients results in a non-effervescent, solid pharmaceutical composition in unit dosage form, that when orally administered to treat symptoms of emesis and related diseases, provides safe and effective absorption and improved bioavailability of ondansetron.

One common form of ondansetron commonly employed in pharmaceutical formulations is the hydrochloride dihydrate. Ondansetron hydrochloride dihydrate can be presented in a variety of formulations such as tablets for oral administration containing 5 mg and 10 mg of ondansetron for the treatment of emesis. These tablets contain ondansetron dihydrate as a racemic mixture which is administered as a hydrochloride salt. The hydrochloride dihydrate form is freely soluble in water and very bitter. Ondansetron can also be employed in free base form in, e.g., 5 mg and 10 mg strength tablets, for the treatment of emesis.

The present invention preferably uses ondansetron in free base form which is soluble in water and tasteless.

In some embodiments, the invention provides a non-effervescent, solid orally disintegrating dosage form adapted for oral administration to a mammal, comprising:
about 1 to about 80% by weight of ondansetron base;
about 1 to about 90% by weight of a hydrophilic component comprising a first water-dispersible component, a component having a —CHOH functional group and a water-insoluble component,
wherein the first water-dispersible component is selected from the group consisting of a water-dispersible cellulose derivative, a water-soluble hydrophilic polymer, and combinations thereof,
wherein the water-insoluble component is selected from the group consisting of a water-insoluble cellulose derivative, croscarmellose sodium, crospovidone, AMBERLITE (Rohm and Haas, Philadelphia, Pa.), calcium silicate, a modified starch, and combinations thereof;
up to 30% by weight of at least one lubricant selected from the group consisting of magnesium stearate, sodium stearyl fumarate, calcium stearate, sodium stearate, stearic acid, talc, hydrogenated vegetable oil, silicon dioxide, and combinations thereof,
wherein the dosage form does not rely upon effervescence for disintegration of the dosage form, and
wherein the dosage form disintegrates in saliva or in water within 60 seconds.

In some embodiments, the component having a —CHOH functional group is selected from the group consisting of mannitol, xylitol, sorbitol, maltitol, lactitol, erythritol, inositol, xylose, arabinose, pentose, galactose, dextrose, sucrose, trehalose, and combinations thereof.

In some embodiments, the water-dispersible cellulose derivative is selected from the group consisting of low molecular weight hydroxypropyl cellulose, low molecular weight methyl cellulose, low molecular weight hydroxypropyl methyl cellulose, and combinations thereof.

In some embodiments, the water-soluble hydrophilic polymer is selected from the group consisting of polyvinyl pyrrolidone, polyethylene glycol, acacia, and combinations thereof.

In some embodiments, the water-insoluble cellulose derivative is microcrystalline cellulose.

In some embodiments, the modified starch is selected from the group consisting of sodium starch glycolate, pregelatinized starch, and combinations thereof.

In some embodiments, the dissolution of the dosage form in a medium containing 500 mL of 0.01 N HCl and a paddle speed of 50 rpm is greater than 75 percent at thirty minutes.

In some embodiments, the dosage form has a hardness ranging from about 0.3 kp to about 5 kp. In some embodiments, the dosage form is a tablet. In some embodiments, the dosage form is an orally disintegrating tablet.

In some embodiments, the invention provides a dosage form, comprising:
about 1 to about 12% by weight of ondansetron base;
about 1 to about 30% by weight of the water-dispersible cellulose derivative selected from the group consisting of low molecular weight hydroxypropyl cellulose, low molecular weight methylcellulose, low molecular weight hydroxypropyl methyl cellulose, and combinations thereof;
about 1 to about 80% by weight of the component having a —CHOH functional group selected from the group consisting of mannitol, xylitol, sorbitol, maltitol, lactitol, erythritol, xylose, arabinose, pentose, galactose, dextrose, inositol, sucrose, trehalose, and combinations thereof;
about 1 to about 40% by weight of the water-insoluble component selected from the group consisting of a microcrystalline cellulose, crospovidone, croscarmellose sodium, AMBERLITE (Rohm and Haas, Philadelphia, Pa.), calcium silicate, sodium starch glycolate, and combinations thereof; and
up to 10% by weight of at least one lubricant selected from the group consisting of magnesium stearate, sodium stearyl fumarate, calcium stearate, sodium stearate, stearic acid, talc, hydrogenated vegetable oil, silicon dioxide and combinations thereof.

A useful embodiment of the present invention comprises:
about 1 to about 12% by weight of ondansetron base;
about 1 to about 10% by weight of a component selected from the group consisting of microcrystalline cellulose, hydroxypropyl cellulose, methylcellulose, and hydroxypropyl methyl cellulose;
about 1 to about 80% by weight of at least one sugar selected from the group consisting of mannitol, xylitol, sorbitol, maltitol, lactitol, erythritol, xylose, arabinose, pentose, galactose, dextrose and mixtures thereof;
about 1 to about 60% by weight of at least one water-insoluble component selected from the group consisting of crospovidone, croscarmellose sodium, sodium starch glycolate, colloidal silicon dioxide and mixtures thereof; and up to 10% by weight of at least one lubricant selected from the group consisting of magnesium stearate, sodium stearyl fumarate, calcium stearate, sodium stearate, stearic acid, talc, hydrogenated vegetable oil, silica gel, such as colloidal silicon dioxide, and mixtures thereof. The silica gel can be, but is not limited to, colloidal silicon dioxide.

Another aspect of the present invention is drawn to dosage forms as described above which include ondansetron; xylitol and/or mannitol as the water-soluble component having a —CHOH functional group; microcrystalline cellulose and crospovidone as the water-insoluble components; povidone as the water-soluble hydrophilic polymer; colloidal silicon dioxide, magnesium stearate and sodium stearyl fumarate as lubricants; and optionally aspartame and strawberry flavor as a sweetener and a flavoring, respectively.

A solid unit dosage can be in the form of a tablet comprising: about 6.7% ondansetron, about 4.2% microcrystalline cellulose, about 25% crospovidone, about 50% mannitol, about 1.25% colloidal silicon dioxide, about 0.8% each of magnesium stearate and sodium stearyl fumarate, about 7.1% xylitol and optionally about 3.33% aspartame and about 0.8% strawberry flavor by total weight of the tablet.

A solid unit dosage can be in the form of a tablet comprising: about 7% by weight ondansetron, about 1.3% by weight colloidal silicon dioxide, about 7% by weight xylitol, about 4% by weight microcrystalline cellulose, about 50% by weight mannitol, about 25% by weight crospovidone, about 0.9% by weight magnesium stearate, and about 0.9% by weight sodium stearyl fumarate.

Among the advantages of the present non-effervescent orally disintegrating tablets are that manufacturing is a continuous process and inexpensive, no special environment conditions are required as compared to freeze-drying in the process, no modification of the crystalline property of the drug is required during manufacturing, the resultant tablets are less sensitive to moisture, conventional tablet machines can be used, there is good scalability and reproducibility of the tablets, and no preservative is required as is the case in the freeze-drying process.

The ratio of active ingredient to excipients in the improved oral solid dosage forms of the invention is from about 1:99 to about 1:1, by weight.

In some embodiments, a compressed tablet can have a hardness of about 0.3 to about 5 kiloponds (kp). In some embodiments, a compressed tablet can have a hardness of about 0.3 to about 3 kp. In some instances, the hardness of the tablet is about 1 kp.

The solid oral dosage forms are preferably tablets. The tablets are in the form of non-effervescent, orally disintegrating tablets which are compressed from a mixture of the dry ingredients. The net weight of a compressed tablet comprising the ondansetron composition of the present invention is from about 30 mg to about 1000 mg. The ondansetron tablets can be made commercially available in tablets of about 60 mg and of about 120 mg, each containing proportional doses of ondansetron.

An additional aspect of the present invention is a method of treating gastrointestinal disorders and diseases or mental disorders including reducing or preventing emesis from cancer chemotherapy and radiation therapy in a human comprising administering the dosage forms of the present invention.

In some embodiments, the invention provides a process of forming a pharmaceutical tablet, comprising mixing:

about 1 to about 80% by weight of ondansetron base;

about 1 to about 90% by weight of a hydrophilic component comprising a first water-dispersible component, a component having a —CHOH functional group and a water-insoluble component, wherein the first water-dispersible component is selected from the group consisting of a water-dispersible cellulose derivative, a water-soluble hydrophilic polymer, and combinations thereof, wherein the water-insoluble component is selected from the group consisting of a water-insoluble cellulose derivative, croscarmellose sodium, crospovidone, AMBERLITE (Rohm and Haas, Philadelphia, Pa.), calcium silicate, a modified starch, and combinations thereof;

up to 30% by weight of at least one lubricant selected from the group consisting of magnesium stearate, sodium stearyl fumarate, calcium stearate, sodium stearate, stearic acid, talc, hydrogenated vegetable oil, silicon dioxide, and combinations thereof, to form a mixture;

compressing the mixture to form a non-effervescent, solid orally disintegrating tablet, wherein the tablet does not rely upon effervescence for disintegration of the tablet, and wherein the tablet disintegrates in saliva or in water within 60 seconds.

A fifth aspect of the present invention is drawn to a process of forming a dosage form comprising ondansetron, microcrystalline cellulose, mannitol, crospovidone, colloidal silicon dioxide such as CAB-O-SIL™ (Cabot Corp., Billerica, Mass.), magnesium stearate, sodium stearyl fumarate, xylitol and optionally aspartame and strawberry flavor as described as described further herein.

BRIEF DESCRIPTION OF THE DRAWINGS/FIGURES

FIG. 1 is a flow chart illustrating a method of making an ondansetron formulation.

Figure 2:
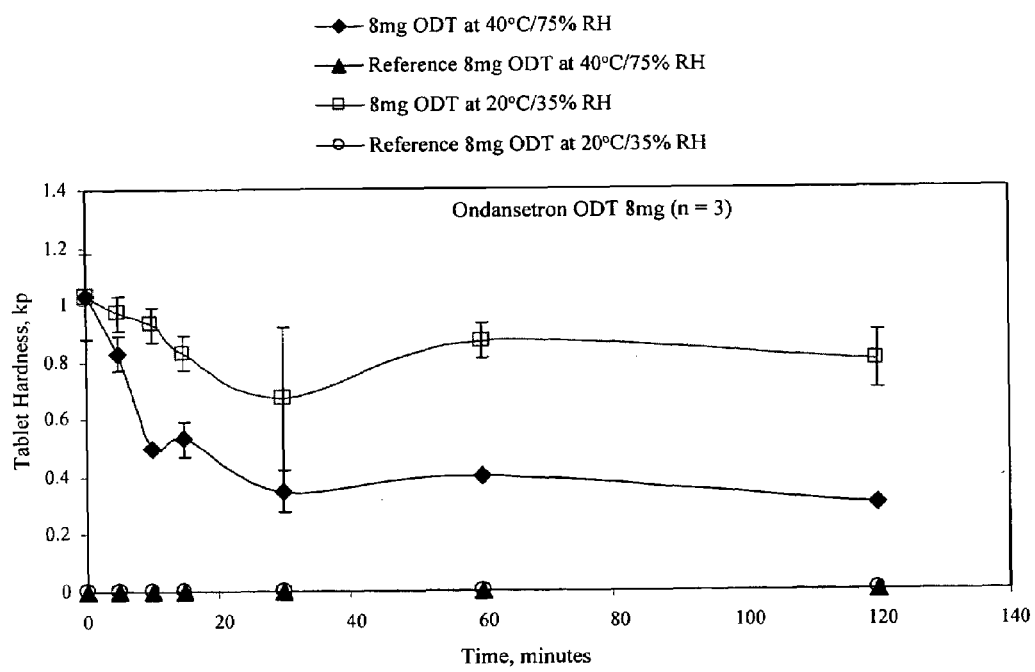

FIG. 2 provides a graph showing hardness of orally disintegrating tablets (ODTs) exposed to storage conditions such as 20° C. and 35% relative humidity (RH), and to conditions such as 40° C. and 75% RH, as a function of time. The graph provides a comparison of the effect of storage conditions on a 8 mg ondansetron ODT formulation of the present invention and a 8 mg reference ondansetron ODT.

Figure 3:
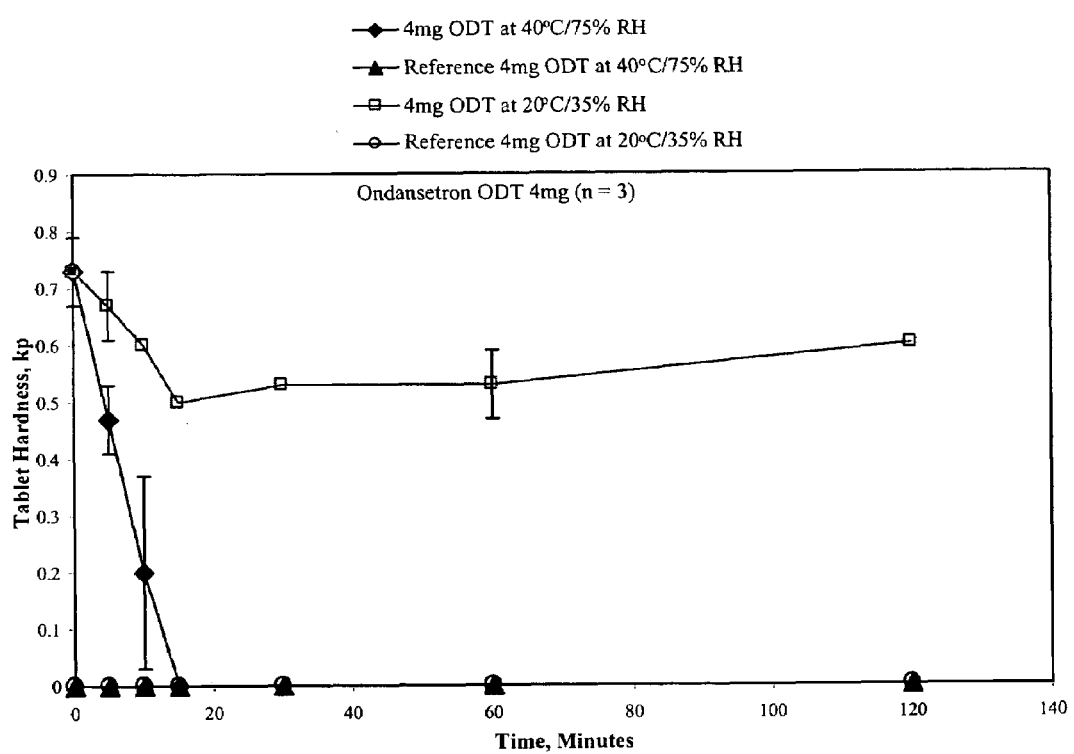

FIG. 3 provides a graph showing hardness of ODTs exposed to storage conditions such as 20° C. and 35% RH, and to conditions such as 40° C. and 75% RH, as a function of time. The graph provides a comparison of the effect of storage conditions on a 4 mg ondansetron ODT formulation of the present invention and a 4 mg reference ondansetron ODT.

Figure 4:
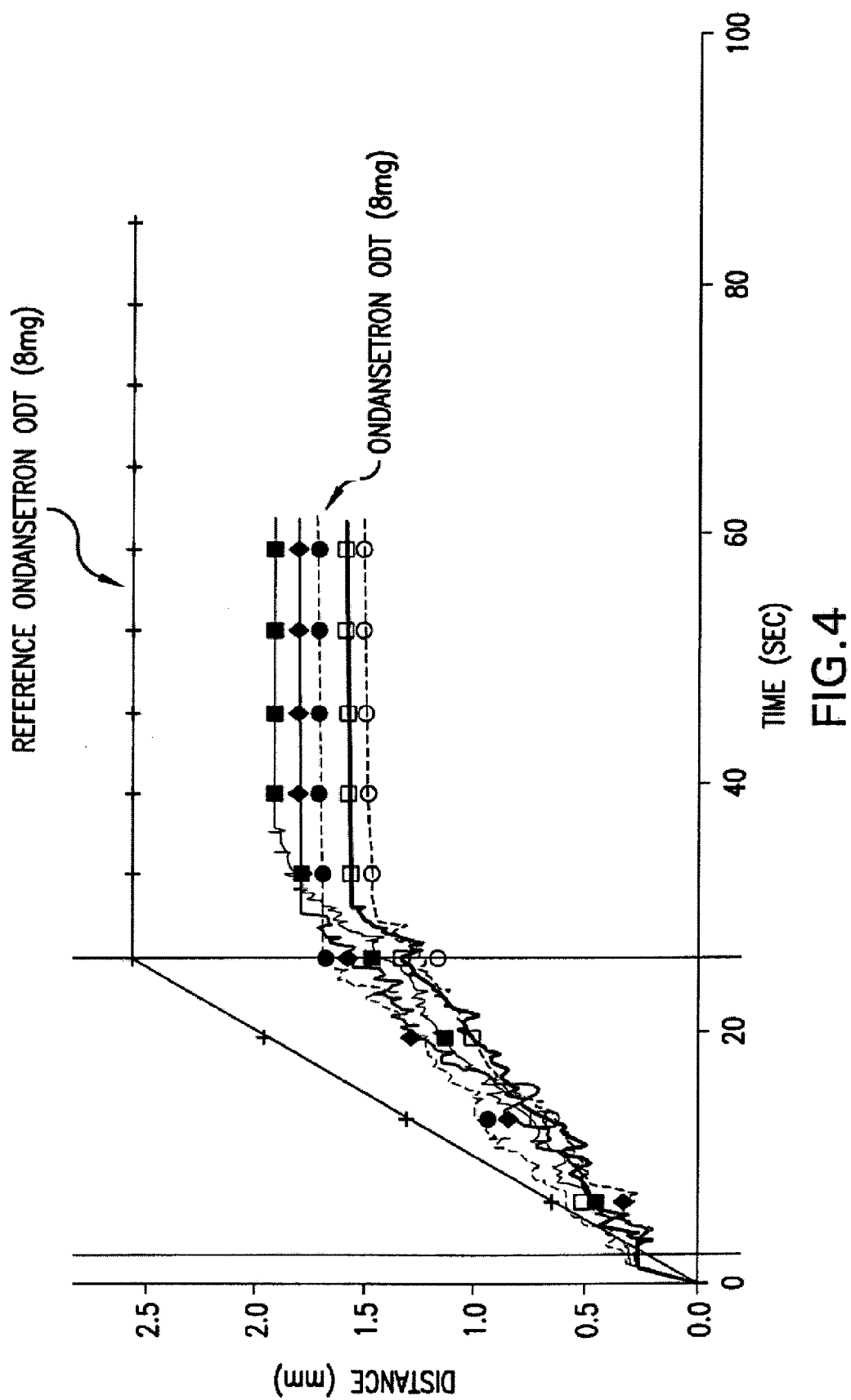

FIG. 4 provides a comparative disintegration profile of a 8 mg ondansetron ODT formulation of the present invention and a 8 mg reference ondansetron ODT tested in 5 ml water at room temperature using a texture analyzer, under conditions of 50 g of probe force and 60 seconds of hold time.

Figure 5:
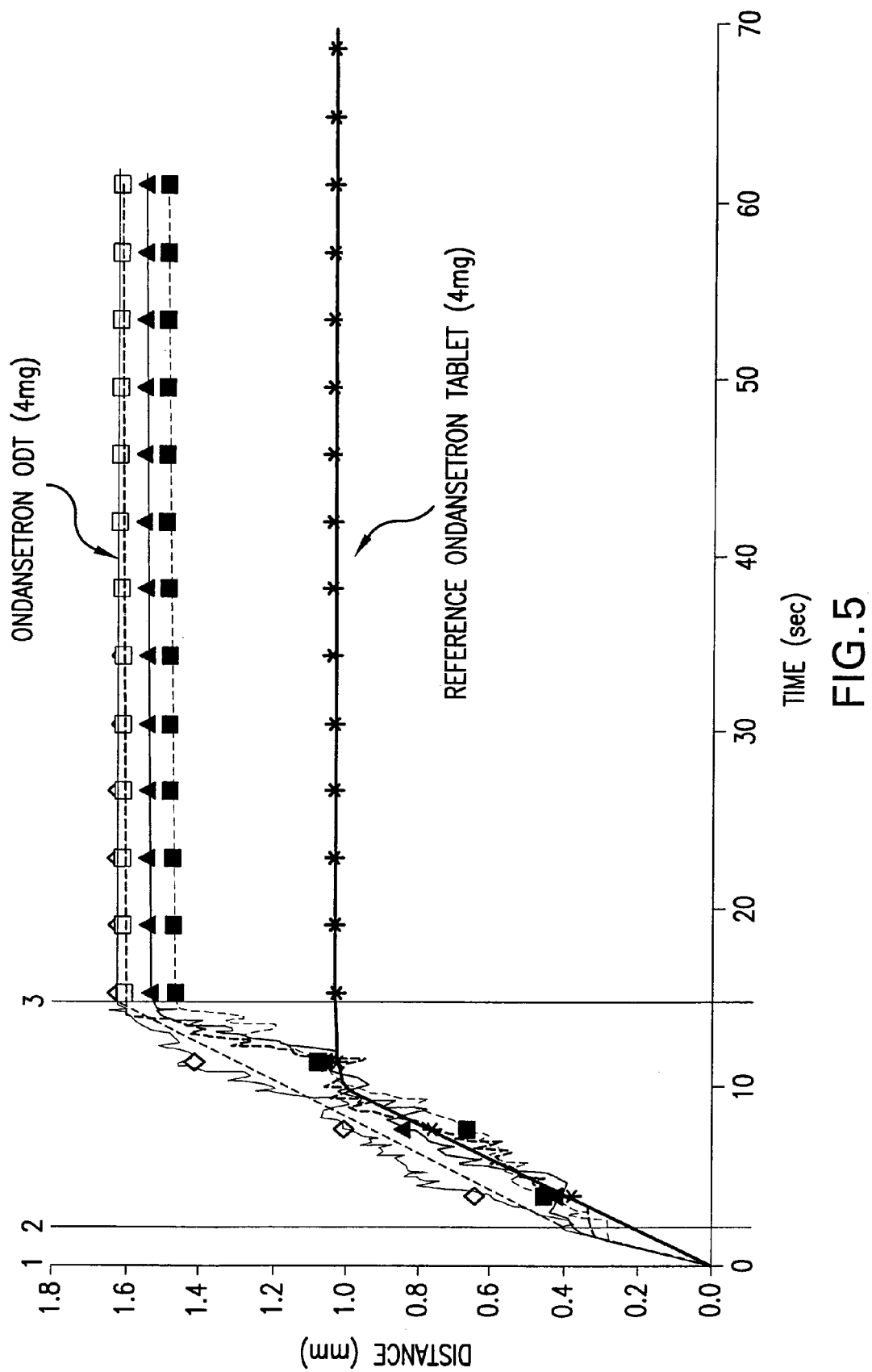

FIG. 5 provides a comparative disintegration profile of 4 mg ondansetron ODTs of the present invention and 4 mg reference ondansetron ODTs that were tested in 5 ml water at room temperature using a texture analyzer, under conditions of 50 g probe force and 60 seconds of hold time.

DETAILED DESCRIPTION OF THE INVENTION

The present invention addresses the problems encountered with currently available technologies by avoiding expensive freeze-drying processes. Moreover, manufacturing the dosage forms of the invention is straight-forward and is suitable for a broad range of active ingredients with different physicochemical parameters, for high dose unit forms (up to, e.g., 1000 mg, in particular 500 mg, of active substance) and also for combinations of active ingredients.

In some embodiments, the invention provides, a non-effervescent, solid dosage form adapted for oral administration having ondansetron as the active ingredient in combination with certain inactive ingredients to treat symptoms of emesis, which provides safe, effective absorption and bioavailability of ondansetron.

Throughout the present document, all expressions of percentage, ratio, corporation, and the like, will be in weight units unless otherwise indicated. The article "a," when employed in the claims, is equivalent to the phrase "one or more" and is not limiting to a single occurrence of the noun that precedes The present invention contemplates oral dosage forms containing ondansetron in free base form. The ondansetron formulations contemplated include a racemic mixture of ondansetron but may comprise ondansetron in an enantiomeric excess or substantially pure enantiomeric form. As will be appreciated by those skilled in the art, salts, hydrates, solvates, and the like could be employed in the present invention, particularly after coating the drug with taste-masking coatings, to obtain the same beneficial effects as that provided by the base form ondansetron. Accordingly, as used herein, the term "ondansetron" contemplates all such forms. In some embodiments, the ondansetron base in the dosage form ranges from about 1% to about 50% by weight. In some embodiments, the ondansetron base in the dosage form ranges from about 1% to about 10% by weight. In some embodiments, the ondansetron base in the dosage form is about 6.7% by weight.

As used herein, the term "pharmaceutically effective amount" refers to an amount of ondansetron which diminishes one or more symptoms of the disease or disorder being treated. For example, a pharmaceutically effective amount for the treatment of emesis caused by cancer chemotherapy refers to the amount which when administered diminishes one or more symptoms associated with emesis caused by cancer chemotherapy. The precise therapeutic dosage of ondansetron necessary to be pharmaceutically active will vary with age, size, sex and condition of the subject, the nature and severity of the disorder or disease to be treated, and the like; thus, a precise pharmaceutically effective amount cannot be specified in advance and will be determined by a caregiver. However, appropriate amounts may be determined by routine experimentation with animal models. In general terms, an effective daily dose is about 10 to 50 milligrams per day per human subject of ondansetron.

The phrase "orally disintegrating" as used herein refers to the ability of the dosage form to disintegrate in saliva or water within 60 seconds. In some embodiments, the dosage form disintegrates in less than 30 seconds.

The term "tablet" as used herein is intended to encompass compressed pharmaceutical dosage formulations of all shapes and sizes, whether coated or uncoated.

As used herein, the term "excipient" refers to the additives used to convert an active compound into a form suitable for its intended purpose. For compositions of the present invention suitable for administration to humans, the term "excipient" is meant to include, but is not limited to, those ingredients described in *Remington: The Science and Practice of Pharmacy*, Lippincott Williams & Wilkins, 21$^{st}$ ed. (2004), which is herein incorporated by reference in its entirety.

In some embodiments, the invention provides a non-effervescent, solid orally disintegrating dosage form adapted for oral administration to a mammal, comprising:

about 1 to about 80% by weight of ondansetron base;

about 1 to about 90% by weight of a hydrophilic component comprising a first water-dispersible component, a component having a —CHOH functional group and a water-insoluble component, wherein the first water-dispersible component is selected from the group consisting of a water-dispersible cellulose derivative, a water-soluble hydrophilic polymer, and combinations thereof, wherein the water-insoluble component is selected from the group consisting of a water-insoluble cellulose derivative, croscarmellose sodium, crospovidone, AMBERLITE, calcium silicate, a modified starch, and combinations thereof;

up to 30% by weight of at least one lubricant selected from the group consisting of magnesium stearate, sodium stearyl fumarate, calcium stearate, sodium stearate, stearic acid, talc, hydrogenated vegetable oil, silicon dioxide, and combinations thereof, wherein the dosage form does not rely upon effervescence for disintegration of the dosage form, and wherein the dosage form disintegrates in saliva or in water within 60 seconds.

In some embodiments, the component having a —CHOH functional group is selected from the group consisting of mannitol, xylitol, sorbitol, maltitol, lactitol, erythritol, inositol, xylose, arabinose, pentose, galactose, dextrose, sucrose, trehalose, and combinations thereof. In some embodiments, the component having a —CHOH functional group ranges from about 1% to about 75%. In some embodiments, the component having a —CHOH functional group ranges from about 1% to about 60%. In some embodiments, the component having a —CHOH functional group ranges from about 1% to about 50%. In some embodiments, the component having a —CHOH functional group ranges from about 1% to about 20%. In some embodiments, the component having a —CHOH functional group component is about 50%. In some embodiments the component having a —CHOH functional group is about 7%. In some embodiments, the water-soluble component having a —CHOH functional group is a combination of mannitol USP available under the trade name PARTECK M-200 (Merck KGaA, Darmstadt, Germany) and xylitol. In some embodiments, the water-soluble component having a —CHOH functional group is mannitol. In some embodiments, the water-soluble component having a —CHOH functional group is xylitol.

In some embodiments, the first water-dispersible component ranges from about 1% to about 50%. In some embodiments, the first water-dispersible component ranges from about 1% to about 15%. In some embodiments, the first water-dispersible component is about 4.1%.

In some embodiments, the water-dispersible cellulose derivative is selected from the group consisting of low molecular weight hydroxypropyl cellulose, low molecular weight methyl cellulose, low molecular weight hydroxypropyl methyl cellulose, and combinations thereof. Preferred molecular weights of low molecular weight hydroxypropyl cellulose and for hydroxypropyl methyl cellulose are molecular weights less than 100,000. For low molecular weight methyl cellulose, the preferred molecular weights are less than 50,000.

In some embodiments, the water-soluble hydrophilic polymer is selected from the group consisting of polyvinyl pyrrolidone, polyethylene glycol, acacia, and combinations thereof. In some embodiments, the water-soluble hydrophilic polymer is polyvinyl pyrrolidone.

In some embodiments, the water-insoluble component ranges from about 1% to about 75%. In some embodiments, the water-insoluble component ranges from about 1% to about 60%. In some embodiments, the water-insoluble component ranges from about 1% to about 50%. In some embodiments, the water-insoluble component ranges from about 1% to about 40%. In some embodiments, the water-insoluble component ranges from about 1% to about 15%. In some embodiments, the water-insoluble component is about 25%. In some embodiments, the water-insoluble component is about 4.1%. In some embodiments, the water-insoluble component is a combination of microcrystalline and crospovidone.

In some embodiments, the water-insoluble cellulose derivative is microcrystalline cellulose. In some embodiments, the water-insoluble cellulose derivative ranges from about 1% to about 50%. In some embodiments, the water-insoluble cellulose derivative ranges from about 1% to about 15%. In some embodiments, the water-insoluble cellulose derivative is about 4.1%.

In some embodiments, the modified starch is selected from the group consisting of sodium starch glycolate, pregelatinized starch, and combinations thereof.

Dissolution analysis can be perfomed, e.g., using a Bankel dissolution apparatus. In some embodiments, the dissolution of the dosage form in a medium containing 500 mL of 0.01 N HCl and a paddle speed of 50 rpm is greater than 75 percent at thirty minutes.

In some embodiments, the dosage form has a hardness ranging from about 0.3 kp to about 5 kp. In some embodiments, the dosage form has a hardness ranging from about 0.3 kp to about 3 kp. In some embodiments, the dosage form has a hardness ranging from about 1 kp.

In some embodiments, the dosage form is a tablet. In some embodiments, the dosage form is an orally disintegrating tablet.

Methods of tablet formulation have been developed in order to impart desirable characteristics to the drug/material(s) to be compressed into a solid dosage form. Usually, the material to be compressed into a solid dosage form includes one or more excipients to impart free-flowing, lubrication, and cohesive properties to the drug(s) which is to be formulated into a dosage form.

Typically, excipients are added to the formulation which impart good flow and compression characteristics to the material as a whole which is to be compressed. Such properties are typically imparted to these excipients via a pre-processing step such as wet granulation, slugging, spray drying, spheronization, or crystallization. Useful direct compression excipients include processed forms of cellulose, components having a —CHOH functional group, and dicalcium phosphate dihydrate, among others.

The pharmaceutically acceptable excipients and additives which may be used in the present invention can include the first water-dispersible components or water-insoluble cellulose derivatives such as calcium carboxymethyl cellulose, other water-insoluble components such as crospovidone, modified starches such as sodium starch glycolate, water-soluble components having a —CHOH functional group, inorganic substances, lubricants, e.g., magnesium stearate, talc, silica gel, such as colloidal or fumed silicon dioxide, sodium stearyl fumarate or valine; a sweetening agent, e.g., aspartame, stevioside; other excipients, e.g., microcrystalline cellulose; and a mixture thereof. Each additive may be used in an amount of 0.1 to 90% by weight or 0.2 to 80% by weight, based on the weight of the composition.

The ondansetron composition of the present invention does not require effervescence to aid in complete disintegration but employs one or more water-insoluble components to facilitate the breakup of the tablet after its administration.

The water-insoluble components ensure that the ultimately prepared compressed solid dosage form has an acceptable disintegration rate in an environment of use (such as the gastrointestinal tract). Typical water-soluble components include starch derivatives, clays, algins, gums, cross-linked polymers and celluloses such as salts of carboxymethyl cellulose.

The water-insoluble components in the present invention can include superdisintegrant agents such as crospovidone, croscarmellose sodium, and sodium starch glycolate. Superdisintegrants are disintegrating agents which require lower levels present in the pharmaceutical composition to be effective as compared to other disintegrating agents. While not wishing to be bound by a specific theory, it is believed that water-insoluble components, such as, calcium silicate, calcium trisilicate, magnesium trisilicate, magnesium silicate, and combinations thereof, might act by facilitating the disintegration action of components such as crospovidone. Water-insoluble components that can be used in the present invention include water-insoluble cellulose derivatives such as microcrystalline cellulose.

A useful pharmaceutical composition of the present invention employs crospovidone. Crospovidone is a water-insoluble synthetic cross-linked homopolymer of N-vinyl-2-pyrrolidinone. Cross-linked polyvinylpyrrolidone (crospovidone), NF is available under the trade name POLYPLASDONE XL (ISP Technologies, Wayne, N.J.).

The components of the present invention are sufficient for complete disintegration without the use of effervescent agents. In determining the disintegration time and profile of the inventive formulation, a disintegration test using a texture analyzer is used, e.g., a TA-XTplus texture analyzer from (Texture Technologies Corporation, Scarsdale, N.Y.). The disintegration time of tablets of the present invention can be about 5 seconds or less when tested in an automated disintegrator tester, e.g., Rwika. Methods of evaluating disintegration behavior are generally disclosed in "Evaluation of disintegration testing of different fast dissolving tablets using the texture analyzer," el-Arini, S K and Clas S D, Pharm. Dev. Technol., 7(3):361-71 (2002). To assist in the cohesion of dry ingredient, it is helpful to include a first water-dispersible component and/or water-insoluble cellulose derivative such as microcrystalline cellulose, hydroxypropyl cellulose, methyl cellulose, hydroxypropyl methyl cellulose and polyvinyl pyrrolidone (povidone). The water-insoluble cellulose derivative can be microcrystalline cellulose, such as, but not limited to, microcrystalline cellulose NF available under the trade name AVICEL PH 101 (FMC BioPolymer, Philadelphia, Pa.).

A cellulose for the present invention can be microcrystalline cellulose. Microcrystalline cellulose, a processed cellulose, has been utilized extensively in the pharmaceutical industry as a direct compression vehicle for solid dosage forms.

Microcrystalline cellulose is commercially available in several grades which range in average particle size from 20 to 200 microns such as under the tradename EMCOCEL™ (Penwest Pharmaceuticals Co. Patterson, N.Y.) and as AVICEL™ (FMC BioPolymer, Philadelphia, Pa.). Compared to other directly compressible excipients, microcrystalline cellulose is generally considered to exhibit superior compressibility and disintegration properties.

The formation of a disintegrating tablet must be made under generally anhydrous conditions. Microcrystalline cellulose also aids in disintegration by swelling or by taking in moisture from the ambient conditions and drawing it into the tablet to aid in dissolving the water soluble components.

Microcrystalline cellulose is water-insoluble, but the material has the wicking ability, whereby the tablets then swell on contact with water or saliva. Thus, microcrystalline cellulose can act as a diluent and as a disintegrating agent.

Typically, microcrystalline cellulose has an apparent density of about 0.28 g/cm$^3$ to about 0.34 g/cm$^3$ and a tap density of about 0.35 g/cm$^3$ to about 0.48 g/cm$^3$ (pages 108-111, Handbook of Pharmaceutical Excipients, 4$^{th}$ Ed., Pharmaceutical Press and The American Pharmaceutical Association, 2003).

A common class of excipients in solid dosage forms are a first-water dispersible component, a water-insoluble cellulose derivative and a component having a —CHOH group such as starch, sucrose, glucose, dextrose or lactose, which impart cohesive qualities to the powdered material(s).

Natural and artificial sweeteners may be used in the present invention. An example of a sweetener which may be used in the present invention is a saccharide having a sweet taste and good solubility in water. Representative sweeteners include aspartame, sucralose, acesulfame potassium, sodium cyclamate, saccharine, lactose, mannitol, sorbitol, xylitol, erythritol, glucose, sucrose, fructose, rebulose, maltodextrin, paratinose, and mixtures thereof. The saccharide may be used in an amount of 10 to 95% by weight, preferably 20 to 90% by weight, based on the weight of the composition.

The dosage forms of the present invention employ a component having a —CHOH functional group, such as, mannitol, xylitol, sorbitol, maltitol, lactitol, erythritol, xylose, arabinose, pentose, galactose, dextrose or mixtures thereof. Certain embodiments of the invention employ mannitol and/or xylitol as the component having a —CHOH functional group. As is known by those skilled in the art, mannitol is primarily used in the pharmaceutical arts as a diluent or filler and contains not less than 96.0% and not more than 101.5% of this sugar having the principle pharmaceutical uses of mannitol are as diluent, sweetening agent and tonicity agent.

Lubricants are typically added to avoid the material(s) being tableted from sticking to the punches. Commonly used lubricants include magnesium stearate, calcium stearate and colloidal silicon dioxide. In some embodiments, lubricants range from about 0.1 to about 6% by weight of the dosage form. In some embodiments, lubricants range from about 0.1 to about 5% by weight of the dosage form. In some embodiments, lubricants range from about 0.1 to about 4% by weight of the dosage form. In some embodiments, lubricants range from about 0.1 to about 3% by weight of the dosage form. In some embodiments, lubricants range from about 0.1 to about 2% by weight of the dosage form. In some embodiments, lubricants are included in the final tableted product in amounts of less than 2% by weight. In some embodiments, lubricants are about 1.25% by weight of the dosage form. In some embodiments, lubricants are about 0.8% by weight of the dosage form. In some embodiments, the lubricants are a combination of colloidal silicon dioxide, magnesium stearate, and sodium stearyl fumarate.

The present invention contemplates the use of hydrophobic lubricants to assist in the removal of tablets from the dies during tablet compression and to reduce the friction of particles. Common hydrophobic lubricants suitable in the present formulation are: magnesium stearate, sodium stearyl fumarate, calcium stearate, sodium stearate, stearic acid, talc, and hydrogenated vegetable oil, and silica gel such as, colloidal silicon dioxide. The presence of at least one of the above mentioned lubricants is contemplated in the present invention. One combination can be magnesium stearate, NF and sodium stearyl fumarate, NF. Sodium stearyl fumarate is commonly available under the tradename PRUV (Penwest Pharmaceuticals Co., Patterson, N.Y.).

In addition to lubricants, solid dosage forms may contain diluents. Diluents are frequently added in order to increase the bulk weight of the material to be tableted in order to make the tablet a practical size for compression. This is often necessary where the dose of the drug is relatively small.

A dosage form of the present invention can include colloidal silicon dioxide. Colloidal silicon dioxide is a submicroscopic fumed silica prepared by the vapor-phase hydrolysis of a silicon compound. When ignited at 1000° C. for two hours, it contains not less than 99.0 and not more than 100.5 percent of $SiO_2$. Colloidal silicon dioxide facilitates tablet disintegration, acts as a lubricant, and helps increase the bulk of the pharmaceutical formulation.

The silicon dioxide utilized in the invention is of the very fine particle size variety. In some embodiments of the invention, the silicon dioxide utilized is a colloidal silicon dioxide. In some embodiments, fumed silicon dioxide is used. Colloidal silicon dioxide is a submicron fumed silica prepared by the vapor-phase hydrolysis (e.g., at 1110° C.) of a silicon compound, such as silicon tetrachloride. The product itself is a submicron, fluffy, light, loose, bluish-white, odorless and tasteless amorphous powder which is commercially available from a number of sources, including Cabot Corporation, Billerica, Mass. (under the tradename CAB-O-SIL); Degussa, Corp., Parsipanny, N.Y. (under the tradename AEROSEL); E.I. DuPont & Co.; and W.R. Grace & Co. Colloidal silicon dioxide is also known as colloidal silica gel, fumed silica, light anhydrous silicic acid, silicic anhydride, and silicon dioxide fumed among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products.

In addition to one or more active ingredients, additional pharmaceutically acceptable excipients can be added to preparation of the final product. For example, if desired, any generally accepted soluble or insoluble inert pharmaceutical excipient material can be included in solid dosage form, such as a monosaccharide, a disaccharide, a polyhydric alcohol, inorganic phosphates, sulfates or carbonates, and/or mixtures thereof. Examples of suitable inert pharmaceutical excipients include sucrose, dextrose, lactose, xylitol, fructose, mannitol sorbitol, calcium phosphate, calcium sulfate, calcium carbonate, "off-the-shelf" microcrystalline cellulose, mixtures thereof, and the like. Excipients for the present invention include xylitol and mannitol.

Inorganic substances may also be included in the dosage form, such as colloidal silicon dioxide, hydrotalcite, aluminum magnesium silicate, aluminum hydroxide, titanium dioxide, talc, aluminum silicate, magnesium aluminum metasilicate, bentonite and a mixture thereof.

In addition to the above-mentioned ingredients, other excipients may be added to the present composition. In particular, coloring agents and flavoring agents may be added. Any coloring suitable for oral ingestion, including natural synthetic coloring such as F.D.& C. dyes, are appropriate in the present invention. A natural or an artificial sweetener may be employed to improve the taste of the tablet upon disintegration, such as aspartame, saccharine, sucralose, acesulfame potassium, sodium cyclamate, saccharine, and combinations thereof. Particular dosage forms include aspartame, saccharine and mixtures thereof. In some embodiments, the artificial sweetener ranges from about 0.1% to about 20% by weight of the dosage form. In some embodiments, the artificial sweetener ranges from about 0.1% to about 10% by weight of the dosage form. In some embodiments, the artificial sweetener ranges from about 0.5% to about 5% by weight of the dosage form. In some embodiments, the artificial sweetener is about 3.5% by weight of the dosage form. In some embodiments, the artificial sweetener is aspartame.

In addition, natural and artificial flavorings may be added to the dosage forms, e.g., strawberry, cherry, almond, citrus fruit, and combinations thereof. Citrus flavorings that can be used include, but are not limited to, orange, tangerine, lemon, lime, lemon-lime, citrus, and the like. In some embodiments, the dosage forms include strawberry flavor. In some embodiments, the flavoring ranges from about 0.1% to about 10% by weight of the dosage form. In some embodiments, the flavoring ranges from about 0.1% to about 4% by weight of the dosage form. In some embodiments, the flavoring ranges from about 0.1% to about 2% by weight of the dosage form. In some embodiments, the flavoring is about 0.8% by weight of the dosage form. In some embodiments, the flavoring is strawberry.

The disclosed ondansetron dosage forms can be prepared as a solid oral dosage form, preferably as tablets for medical administration. The dosage form can be provided as a non-effervescent, orally disintegrating tablet compressed from a mixture of the dry ingredients. The net weight of a compressed tablet comprising the ondansetron composition of the present invention is from about 30 mg to about 1000 mg.

The ondansetron dosage form can be made commercially available in two tablets, one about 60 mg and the other about 120 mg, each containing about 4 mg and about 8 mg doses of ondansetron respectively.

Some embodiments of ondansetron dosage formulations are shown in Table 1.

TABLE 1

Ondansetron Formulations

| Ingredient | % | Preferable Ranges (%) | More Preferable Ranges (%) | Most Preferable Ranges (%) |
|---|---|---|---|---|
| Ondansetron Base | 6.7 | 1-80 | 1-50 | 1-10 |
| Microcrystalline cellulose, NF (AVICEL PH 101) | 4.1 | 1-90 | 1-50 | 1-15 |
| Strawberry Flavor (Powder) | 0.8 | 0.1-10 | 0.1-4 | 0.1-2 |
| Crospovidone, NF (POLYPLASDONE XL) | 25 | 1-90 | 1-60 | 1-40 |
| Mannitol USP (PARTECK M 200) | 50 | 1-90 | 1-75 | 1-60 |
| Colloidal Silicon Dioxide, NF (CAB-O-SIL) | 1.25 | 0.1-6 | 0.1-4 | 0.1-2 |
| Magnesium stearate, NF | 0.8 | 0.1-5 | 0.1-3 | 0.1-2 |
| Sodium stearyl fumarate, NF | 0.8 | 0.1-6 | 0.1-4 | 0.1-2 |
| Xylitol (XYLISORB ® 300) | 7 | 1-90 | 1-50 | 1-20 |
| Aspartame, USP (NUTRA SWEET POWDER) | 3.5 | 0.1-20 | 0.1-10 | 0.5-5 |
| Total (%) | 100 | 100 | 100 | 100 |

A solid unit dosage of the pharmaceutical composition of the present invention is prepared by a direct mixing granulation process or a wet-granulation process. The pharmaceutical composition is then compressed into tablets by means known in the art.

A process for forming a tablet of the pharmaceutical composition of the present invention includes mixing the active ingredient, ondansetron, with one or more hydrophilic components at low-speed in a low-shear mixer such as a V-blender, e.g., from Patterson-Kelley. A flavoring and/or a sweetener can subsequently be added to the resulting mixture and blended, followed by adding and mixing silicon dioxide and one or more lubricants to obtain a powder blend. The powder blend can be passed through a screen, compressed into tablets and packaged.

One aspect of this invention is directed to a method of treating and or preventing these diseases by administration to a human subject of the ondansetron formula of the present invention. The administration of the ondansetron composition of the present invention may be administered alone or in conjunction with SSRIs, other antiemetic medications or pain relieving medications.

The dosage forms of the present invention are useful in the therapeutic treatment for patients suffering from emetic disorders. In addition, the disclosed ondansetron compositions can be used to treat other disorders and diseases currently being treated by known antiemetics.

The following examples of processing conditions and parameters are given for the purpose of illustrating the present invention and shall not be construed as being limitations on the scope or spirit of the invention.

EXAMPLES

Example 1

FIG. 1 is a flow chart describing the process for making an ondansetron formulation of the invention. Mannitol and xylitol were combined in a 3 cubic foot V-blender for five minutes with the intensifier bar on. The mixture was then milled through a FITZMILL fitted with a 1522-033 screen and a hammer forward. The mixture is then combined with ondansetron base and AVICEL PH 101 (FMC BioPolymer, Philadelphia, Pa.) and mixed again in the V-blender with the intensifier bar on. After 15 minutes, crospovidone is added and the mixture is blended for another 15 minutes with the intensifier bar off. Aspartame and strawberry flavor is then added to the mixture and mixed for 15 minutes with the intensifier bar off. The mixture is then screened through #20 mesh RUSSELL FINEX (Russel Finex Inc., Pineville, N.C.) screen and then blended for another 6 minutes with the intensifier bar off. Sodium stearyl fumarate, CAB-O-SIL (Cabot Corp., Billerica, Mass.) and magnesium stearate is subsequently added, the powder blend passed through a #30 mesh RUSSELL FINEX screen (Russel Finex Inc., Pineville, N.C.) and the mixing continued for six more minutes with the intensifier bar off. The mixture is then pressed into tablets on a KIKUSUI press (Kikusui Tablet Press, Toms River, N.J.), using 9/32-inch and 12/32-inch FFBE tooling for 4 mg and 8 mg ondansetron tablets respectively. Thereafter, the ondansetron tablets are packaged into aluminum cold peelable blisters of ten tablets. A batch size of 30 kg was used to produce 250,000 tablets containing the 8 mg of ondansetron in the formulation or 500,000 tablets containing 4 mg of ondansetron in the formulation.

Example 2

The procedure of Example 1 was used to make the following 4 mgODT:

TABLE 2

4 mg ODT formulation

| Ingredient | Milligrams/Tablet |
|---|---|
| Ondansetron | 4 mg |
| Xylitol | 4.25 mg |
| Microcrystalline Cellulose | 2.5 mg |
| Colloidal Silicon Dioxide, NF (CAB-O-SIL) | 0.75 |
| Aspartame, USP (NUTRASWEET Powder) | 2.0 mg |
| Natural & Strawberry Flavor Powder | 0.5 mg |
| Mannitol USP (PARTECK M 200) | 30 mg |
| Crospovidone, NF (POLYPLASDONE XL) | 15 mg |
| Magnesium Stearate, NF | 0.5 mg |
| Sodium Stearyl Fumarate, NF | 0.5 mg |
| Net Tablet weight | 60 mg |

Example 3

The procedure of Example 1 was also used to make the following 8 mg ODT:

TABLE 3

8 mg ODT formulation

| Ingredient | Milligrams/Tablet |
|---|---|
| Ondansetron | 8 mg |
| Xylitol | 8.5 mg |
| Microcrystalline Cellulose | 5.0 mg |
| Colloidal Silicon Dioxide, NF (CAB-O-SIL) | 1.5 |
| Aspartame, USP (NUTRASWEET Powder) | 4.0 mg |
| Natural & Strawberry Flavor Powder | 1.0 mg |
| Mannitol USP (PARTECK M 200) | 60 mg |
| Crospovidone, NF (POLYPLASDONE XL) | 30 mg |
| Magnesium Stearate, NF | 1.0 mg |
| Sodium Stearyl Fumarate, NF | 1.0 mg |
| Net Tablet weight | 120 mg |

Example 4

Table 4 provides the effect of exposure conditions on hardness of the 4 mg tablets prepared in Example 2. The tablets of Example 2 were removed from a blister pack and exposed to 20° C. and 35% RH and 40° C. and 75% RH, respectively. The effect of similar exposure on reference 4 mg ODT tablets is also provided in Table 4. As seen in Table 4, the tablets of Example 2, which do not rely upon effervescence for disintegration of the tablet, had a hardness of about 0.73 kp.

TABLE 4

Effect of exposure conditions on hardness of ODT containing 4 mg of ondansetron

| | Barr's 4 mg ODT | | Reference 4 mg ODT | |
|---|---|---|---|---|
| Time (Hours) | 20° C./ 35% RH | 40° C./ 75% RH | 20° C./ 35% RH | 40° C./ 75% RH |
| 0 | 0.73 ± 0.06 | 0.73 ± 0.06 | 0 | 0 |
| 0.25 | 0.67 ± 0.06 | 0.47 ± 0.06 | 0 | 0 |
| 0.5 | 0.6 ± 0 | 0.2 ± 0.17 | 0 | 0 |
| 0.75 | 0.5 ± 0 | 0 | 0 | 0 |
| 1.0 | 0.53 ± 0.06 | | 0 | 0 |
| 2.0 | 0.53 ± 0.06 | | 0 | 0 |
| 24 | 0.6 ± 0 | | 0 | 0 |

Example 5

Table 5 provides the effect of exposure conditions on hardness of the 8 mg tablets prepared in Example 3. The tablets of Example 3 were removed from a blister pack and exposed to 20° C. and 35% RH and 40° C. and 75% RH, respectively. The effect of similar exposure on reference 8 mg ODT tablets is also provided in Table 5. As seen in Table 5, the tablets of Example 3, which do not rely upon effervescence for disintegration of the tablet, had a hardness of about 1 kp.

TABLE 5

Effect of exposure conditions on hardness of ODT containing 8 mg of ondansetron

| | Barr's 8 mg ODT | | Reference 8 mg ODT | |
|---|---|---|---|---|
| Time (Hours) | 20° C./ 35% RH | 40° C./ 75% RH | 20° C./ 35% RH | 40° C./ 75% RH |
| 0 | 1.03 ± 0.15 | 1.03 ± 0.15 | 0 | 0 |
| 0.25 | 0.97 ± 0.06 | 0.83 ± 0.06 | 0 | 0 |
| 0.5 | 0.93 ± 0.06 | 0.5 ± 0 | 0 | 0 |
| 0.75 | 0.83 ± 0.06 | 0.53 ± 0.06 | 0 | 0 |
| 1.0 | 0.67 ± 0.25 | 0.35 ± 0.07 | 0 | 0 |
| 2.0 | 0.87 ± 0.06 | 0.4 ± 0 | 0 | 0 |
| 24 | 0.8 ± 0.1 | 0.3 ± 0 | 0 | 0 |

Example 6

An in vitro dissolution study of the tablets prepared in Examples 2 and 3 was performed using a USP 1 apparatus in a medium of 500 mL of 0.01 N HCl and a paddle speed of 50 rpm. About 100% of the tablet dissolved in five minutes.

Example 7

Disintegration analysis of the tablets of Examples 2 and 3 was performed using a texture analyzer and an automated disintegration tester (DT). Results are provided in Table 6.

TABLE 6

Disintegration analysis of ondansetron ODT

| Tablet strength (mg) | Disintegration on set time (sec) | | Disintegration Rate (mm/sec) | | Extrapolated disintegration time (sec) | | Disintegration time using automated DT | |
|---|---|---|---|---|---|---|---|---|
| | ODT (Barr) | Reference ODT | ODT (Barr) | Reference ODT | ODT (Barr) | Reference ODT | ODT (Barr) | Reference ODT |
| 4 | 2.83 ± 0.6 | 0.01 | 0.1 ± 0.01 | 0.097 | 11.49 ± 0.6 | 10.34 | <5 sec | <5 sec |
| 8 | 3.82 ± 1.5 | 0.17 | 0.05 ± 0.01 | 0.099 | 26.69 ± 3.9 | 25.54 | <5 sec | <5 sec |

While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A non-effervescent, orally disintegrating, solid dosage form comprising:
    ondansetron in a concentration of about 1 to about 10% by weight of said dosage form;
    mannitol in a concentration of about 1% to about 60% by weight of said dosage form;
    xylitol in a concentration of about 1% to about 20% by weight of said dosage form;
    crospovidone in a concentration of about 1% to about 40% by weight of said dosage form;
    microcrystalline cellulose in a concentration of about 1% to about 10% by weight of said dosage form; and
    a hydrophobic lubricant in a concentration of up to about 10% by weight of said dosage form;
    wherein said dosage form is not freeze-dried; and
    wherein the time taken for disintegration of the dosage form in water or in saliva is within 60 seconds.

2. A non-effervescent, orally disintegrating, solid dosage form comprising:
    ondanestron in a concentration of about 7% by weight of said dosage form;
    mannitol in a concentration of about 50% by weight of said dosage form;
    xylitol in a concentration of about 7% by weight of said dosage form;
    crospovidone in a concentration of about 25% by weight of said dosage form;
    microcrystalline cellulose in a concentration of about 4% by weight of said dosage form; and
    a hydrophobic lubricant in a concentration up to about 10% by weight of said dosage form;
    wherein said dosage form is not freeze-dried; and
    wherein the time taken for disintegration of the dosage form in water or in saliva is within 60 seconds.

3. The non-effervescent, orally disintegrating, solid dosage form of claim 1, further comprising a sweetener selected from the group consisting of:
    aspartame, sucralose, acesulfame potassium, sodium cyclamate, saccharine, lactose, sorbitol, erythritol, glucose, sucrose, fructose, rebulose, maltodextrin, paratinose, and combinations thereof.

4. The non-effervescent, orally disintegrating, solid dosage form of claim 1, further comprising an artificial sweetener selected from the group consisting of: aspartame, sucralose, acesulfame potassium, sodium cyclamate, saccharine, and combinations thereof.

5. The non-effervescent, orally disintegrating, solid dosage form of claim 1, further comprising a flavoring selected from the group consisting of:
    strawberry, cherry, almond, lemon, lime and citrus fruit, and combinations thereof.

6. The non-effervescent, orally disintegrating, solid dosage form of claim 1, wherein said dosage form has a hardness of about 0.3 kiloponds to about 5 kiloponds.

7. The non-effervescent, orally disintegrating, solid dosage form of claim 1, wherein said dosage form has a hardness of about 0.3 to about 3 kiloponds.

8. The non-effervescent, orally disintegrating, solid dosage form of claim 1, wherein the time taken for disintegration of the dosage form in water or in saliva is less than 30 seconds.

9. The non-effervescent, orally disintegrating, solid dosage form of claim 1, wherein said dosage form is a tablet.

10. The non-effervescent, orally disintegrating, solid dosage form of claim 1, wherein the dissolution of the dosage form in a medium containing 500 mL of 0.01 N HCl and a paddle speed of 50 rpm is greater than 75 percent at thirty minutes.

11. The non-effervescent, orally disintegrating, solid dosage form of claim 1, wherein the hydrophobic lubricant is selected from the group consisting of: magnesium stearate, sodium stearyl fumarate, calcium stearate, sodium stearate, stearic acid, talc, hydrogenated vegetable oil, colloidal silicon dioxide, and combinations thereof.

* * * * *